United States Patent [19]
Gorsuch et al.

[11] Patent Number: 5,980,478
[45] Date of Patent: Nov. 9, 1999

[54] APPARATUS AND METHOD FOR THE TREATMENT OF ACUTE AND CHRONIC RENAL DISEASE BY CONTINUOUS PASSIVE PLASMA ULTRAFILTRATION

[75] Inventors: Reynolds G. Gorsuch, Yountville, Calif.; Kris Venkat, Somerset, N.J.

[73] Assignee: Transvivo, Inc., Napa, Calif.

[21] Appl. No.: 08/949,055

[22] Filed: Oct. 10, 1997

[51] Int. Cl.[6] .................................................. A61M 37/00
[52] U.S. Cl. ................................ 604/4; 623/12; 604/408; 604/7
[58] Field of Search ...................... 604/4, 408, 7; 623/12

[56] References Cited

U.S. PATENT DOCUMENTS

| | | | |
|---|---|---|---|
| 3,878,564 | 4/1975 | Yao et al. ......................................... 3/1 |
| 4,382,445 | 5/1983 | Sommers ...................................... 604/8 |
| 4,493,696 | 1/1985 | Uldall .......................................... 604/43 |
| 4,552,552 | 11/1985 | Polaschegg et al. ......................... 604/4 |
| 4,769,037 | 9/1988 | Midcalf ....................................... 623/12 |
| 4,898,669 | 2/1990 | Tesio ....................................... 210/232 |
| 4,950,224 | 8/1990 | Gorsuch et al. . |
| 5,002,054 | 3/1991 | Ash et al. ................................. 128/635 |
| 5,053,023 | 10/1991 | Martin ....................................... 604/43 |
| 5,151,082 | 9/1992 | Gorsuch et al. . |
| 5,152,743 | 10/1992 | Gorsuch et al. . |
| 5,224,926 | 7/1993 | Gorsuch et al. . |
| 5,300,086 | 4/1994 | Gory et al. ............................... 606/200 |
| 5,735,809 | 4/1998 | Gorsuch ........................................ 604/4 |
| 5,755,790 | 5/1998 | Chevillon et al. ......................... 623/12 |
| 5,785,700 | 7/1998 | Olson ....................................... 604/408 |

*Primary Examiner*—Ronald Stright
*Assistant Examiner*—Cheryl L. Huseman
*Attorney, Agent, or Firm*—Knobbe, Martens, Olson & Bear, LLP

[57] ABSTRACT

An apparatus for treatment of acute and chronic renal disease by continuous passive plasma ultrafiltration includes a plasmapheresis element comprising a catheter and a plasmapheresis filter element secured to the end of the catheter for being implanted in a patient's vena cava or jugular vein, a tube secured to the catheter for receiving and directing blood plasma, a one-way valve for preventing fluid flow from the tube to the catheter, and a container for receiving and collecting the blood plasma. The treatment of the patient is performed by implanting the catheter and plasmapheresis filter element in a patient's vena cava, passing of blood plasma containing the toxins to be removed from the patient's blood supply through the filter element and along the catheter, and collecting and discarding the collected blood plasma.

42 Claims, 2 Drawing Sheets

APPARATUS AND METHOD FOR THE TREATMENT OF ACUTE AND CHRONIC RENAL DISEASE BY CONTINUOUS PASSIVE PLASMA ULTRAFILTRATION

BACKGROUND OF THE INVENTION

Hemodialysis is well-known and often the prescribed therapy modality for kidney failure, as opposed to kidney transplantation, but has the disadvantage of requiring removing blood from the patient's vasculature, treating the blood ex-vivo by dialysis and/or ultrafiltration to remove the toxins and then return the blood to the patient's body. The substantial disadvantages of hemodialysis, both to the patient and the care giver, include frequent vascular access, coagulation in extracorporeal circuits, susceptibility to infections, hemolyses, "peaks and valleys syndrome", heavy high tech apparatus, patient immobility and extensive required medical supervision and care, as well as the extremely high costs. Although recent advances in acute hemodialysis using renal replacement therapy techniques in which continuous ex-vivo ultrafiltration is emphasized show improvements, the removal of whole blood still has grave disadvantages.

In U.S. Pat. Nos. 4,950,224, 5,152,743 and 5,151,082 there are disclosed methods and apparatus for carrying out in vivo plasmapheresis for separating plasma from other blood components within the body and blood vessels of the patient. The apparatus uses pumping means to motivate the flow of fluid from within the in vitro system, whereby blood plasma is pumped from the patient to a treatment means, such as a dialyzer apparatus in which toxic metabolic waste in the plasma is removed. After the dialysate is treated for removal of the waste products and toxins, the regenerated dialysate, i.e., the treated plasma, is returned and reintroduced to the patient's blood stream. Such methods are referred to as plasma dialysis. The methods and apparatus described in the aforesaid patents are incorporated herein by reference.

As advantageous as plasma dialysis methods are, the treatment and apparatus used are unavailable and/or impractical for patients in third world countries or in less privileged environments which do not have extensive medical support infrastructure for purchasing, using, maintaining or managing such systems and methods of use.

SUMMARY OF THE INVENTION

The present invention relates to in vivo plasmapheresis using continuous passive ultrafiltration in which the ultrafiltrate containing the toxins is collected in a container and discarded. The ultrafiltrate is the portion of blood plasma containing the toxins normally removed by a healthy kidney. There is no dialysis of the extracted plasma and none of the fluid (dialysate) removed from the patient is returned. Thus, there is no requirement of purchasing and maintaining dialysis equipment nor the need of medical technicians for administering dialysis and operating such equipment. Fluid makeup to replace the fluid volume removed from the patient is achieved by oral intake, and, if required by fluid infusion where the amount of fluid makeup for the individual patient exceeds reasonable oral intake alone. Such a system and method may be referred to as plasma ultrafiltration therapy (PUT). The apparatus as well as the method of use will be described in detail hereinafter.

DETAILED DESCRIPTION OF THE PREFERRED EMBODIMENTS

Figure 1:
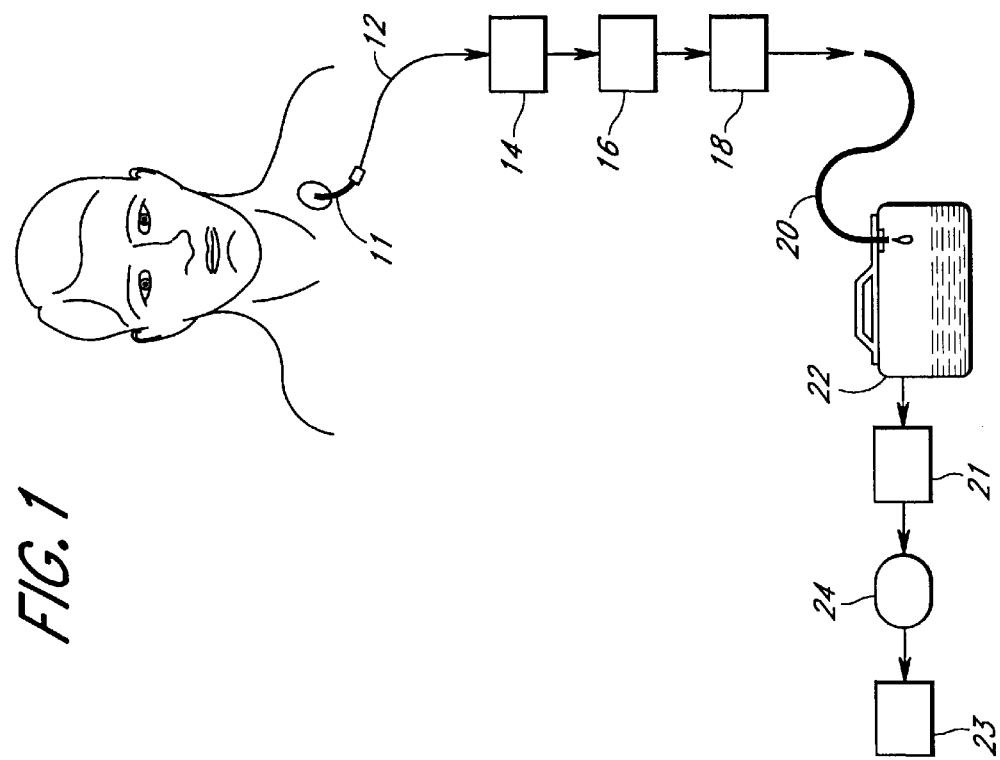
FIG. 1 is a schematic view of a first embodiment of the PUT apparatus assembly illustrating a single lumen catheter configuration.

The PUT system assembly illustrated in FIG. 1 includes a single lumen catheter 11 implanted subcutaneously into a patient's vessel or artery. The catheter is made of a biocompatible material such as polyurethane, of a suitable size. A #6F is typical for a 50–60 kg patient, although larger or smaller catheters may be used depending on the patient's prescription. A plasmapheresis element 30 (see FIG. 3) is permanently attached adjacent to or at the end of catheter 11 and is implanted subcutaneously into the superior vena cava via the internal jugular vein whereby the element resides just above the right atrium.

The plasmapheresis element may be a hollow fiber membrane assembly such as disclosed in the aforesaid patents or in U.S. Pat. No. 5,735,809 issued Apr. 7, 1998, and incorporated herein by reference, or a sheet membrane assembly such as disclosed in co-pending Application Ser. No. 08/935, 399 filed Sep. 23, 1997, also incorporated herein by reference. As used herein, blood plasma or plasma is intended to refer to any segment or portion of plasma that contains the toxins normally removed by the kidneys. A preferred plasmapheresis element comprises hollow elongated microporous fibers or microporous filter sheet membrane assembly having pore openings of a size sufficient to allow passage of the blood plasma as well as toxins contained in the plasma such as specifically described in the aforesaid patents, and particularly U.S. Pat. Nos. 5,224,926 and 5,735, 809. In the latter, preferred catheters include a circumferential fan-like assembly of elongated microporous hollow polymeric fiber loops communicating with the lumen of the catheter, and having a transmembrane flux 1–15 ml/min/cm$^2$ ($H_2O$)/bar. The preferred element also has a total of 100–500 cm$^2$ of outer surface area with a sieving coefficient cutoff of between $2\times10^4$ and $4\times10^6$ daltons. Such a membrane prevents bacteria or large virus from transporting from the patient out and also from the outside of the element to the inner lumens of the catheter. The polymer used in the microporous fibers or membranes may be polypropylene, polyurethane, or other suitable biocompatible material.

In FIG. 1, a single lumen catheter is used in which only plasma is removed from the patient and nothing is returned or infused. In the FIG. 2 embodiment, a dual lumen catheter 25 also provides for the infusion of make-up fluid. In both embodiments, the catheter is professionally implanted subcutaneously into the patient's blood vessel, artery or vein, using surgical procedures known in the art. The catheter is preferably coated with a siloxane composition or a silver coating using plasma polymerization processes in a vacuum to improve smoothness, lubricity, biocompatibilty as well as to prevent bacteria colonization. Such coatings are also known to resist clot formations on their surface for extended periods of implantation as well as for reducing adsorption of proteins on the catheter surface. The entire surface of the catheter and plasmapheresis element may also be coated with a covalently bonded heparin also used for improving anti-clot performance. Further, other current state of art coating such as polytheleneglycol derivatives and/or hydrogels may be used to prevent protein adhesion to the device. The plasmapheresis element also preferably includes a fibrous cuff 26 (FIG. 3) at the subdermal interface of the catheter which provides a substrate for epidural tissue ingrowth. Such ingrowth forms a barrier at the epidermal layer for preventing external bacterial and foreign matter invasion.

Figure 2:
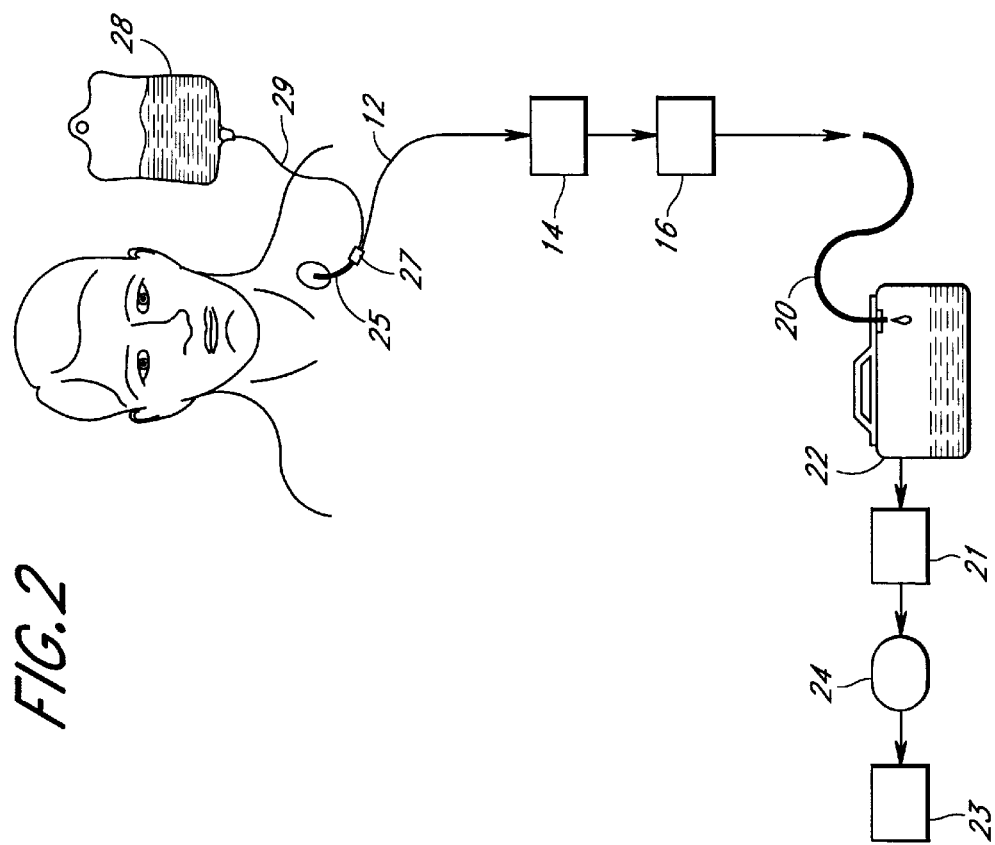
FIG. 2 shows a second embodiment of the PUT system using a dual lumen catheter and means for permitting makeup fluid infusion to the patient.

As shown in both FIGS. 1 and 2, a fluid conducting tube 12, preferably comprising a flexible plastic material is attached to the external catheter using a suitable adapter, such as a Luer lock-type device which prevents inadvertent, accidental or unintended disconnection between the plastic tube 12 and the catheter 11, 25. However, any other suitable connection member or means known to those skilled in the art, preferably satisfying Luer standards may be used. Such devices may be of the quick-disconnect or threaded type locking mechanisms, to facilitate replacement, repair and/or cleaning of the tubing without otherwise disturbing the implanted plasmapheresis filter and catheter element. The tube 12 is also preferably provided with a one-way or check valve 14 to prevent fluid from returning to the plasmapheresis element and the patient, and an emergency vacuum release valve 18 to terminate plasma flow if excessive transmembrane pressure is applied, by releasing the vacuum to atmosphere. The assembly also preferably includes a variable flow control device 16 to permit the patient to limit the flow rate of plasma exudate. Such a flow rate control device may be of any type of fluid flow limiter for example, a variable orifice critical flow device. A flow rate meter may also be incorporated to assist the patient or therapist in monitoring and adjusting the plasma flow rate. The use of a flow rate device offers the advantage of allowing the system to be adapted to the lifestyle and/or needs of the patient. For example, a patient could operate the system at one flow rate during periods of physical activity and another flow rate during inactive rest or sleep periods. Such flexibility thus emulates the physiology of the patient where normal kidney function is ordinarily depressed during sleep hours and accelerated during periods of increased activity when oral fluid intake is also usually greater.

A drain bag or collection container 22, preferably having incompressible walls, communicates with the end of tube 12 for receiving and collecting the plasma exudate. The container is preferably provided with printed volume lines on its surface and a stop cock for selective disposal of the contents. A syphon loop 20, preferably built-in, may be used to communicate the container 22 with the distal end of the tube 12. The use of a syphon loop ensures a vacuum lock regardless of the attitude of the components of the system. Thus, with all of the components of the system in vacuum lock communication, i.e., connected together so that there is no loss of the vacuum between the container 22 and the plasmapheresis element, continued and controlled flow of the plasma exudate from the patient is assured. Since a standard foot of water produces a negative pressure (vacuum) of 0.029 bar, wearing the container at a distance of about 2 feet (60 cm) of vertical distance from the vena cava level will provide adequate pressure differential across the catheter extraction element for up to 50% degradation of the membrane flux specification over the long term due to any cause. Where it is impractical or inconvenient for a patient to wear the collection container two feet below the extraction element level, a manually operated vacuum pump may be used and attached to the collection bag 22 in lieu of the syphon mechanism for creating negative differential pressure across the plasma extraction membrane. The substitute system comprises a hand vacuum pump such as a rubber bulb or bellows 24 with check valves 21–23 on each side of the bellows, and connected to an uncollapsible segment of the collection container. The vacuum created by such a pump device can be regulated by observing flow rate of the plasma entering the container and/or by use of a simple vacuum gauge. The size and shape of the container may be selected depending on the patient's needs. A two liter rigid plastic container may be suitable for most patents.

Figure 3:
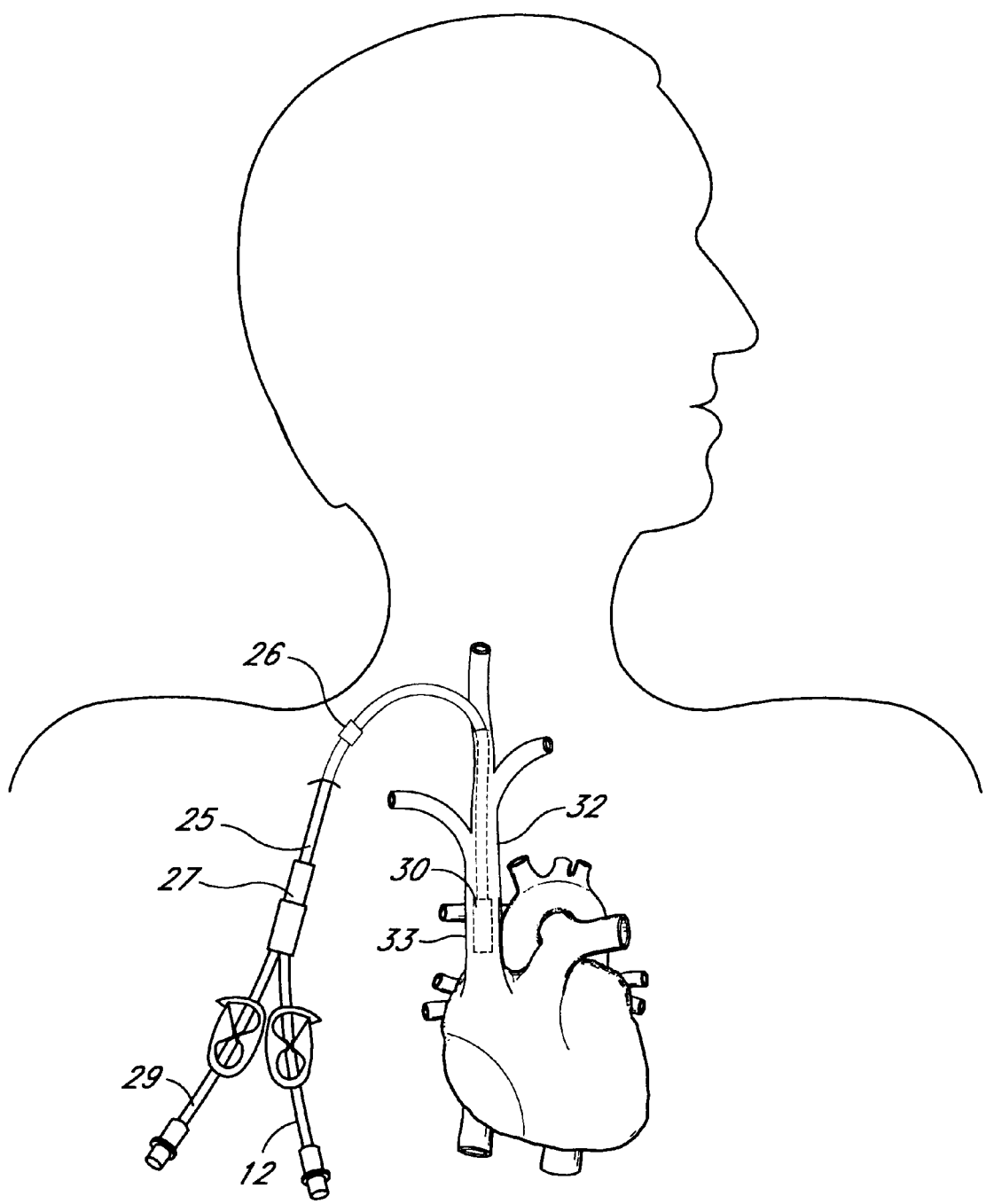
FIG. 3 illustrates location and positioning of the implanted plasmapheresis component of the PUT system of the invention.

In FIG. 2, the use of a dual lumen catheter 25 is shown which provides a second channel permitting makeup fluids to be infused to the patient. Such fluids may also include antibiotics, parenteral feeding therapy fluids, and the like. Dual lumen catheters are well known and clearly described in the aforesaid patents. External to the patient, the catheter is split into two segments as also illustrated in FIG. 3. Inlet conduit 29 may be connected to the infusion bag 28 through an adapter 27, which may include a Luer-type fitting. The inlet conduit 29 is also preferably provided with a bacteria filter to prevent bacteria and virus from entering the body through that path, and may be permanently attached to the infusion bag 28. A one-way or check valve is also preferably used with the inlet source. A flow control device may also be incorporated in the conduit 29 or adapter 27 where the fluid is to be infused by gravity flow, although an infusion pump may be used if affordable. Any flow control means typically or commonly used by those in the art, such as a drip chamber and tube occluder may also be used. Fluid infusion will normally be performed during the patient's inactive or rest period. Otherwise, the embodiment illustrated in FIG. 2 is substantially like that of FIG. 1 regarding continuous flow, collection and discarding of plasma flow as previously described.

In FIG. 3, the positioning of the plasmapheresis element including the catheter 25 and filter element 30 through the jugular vein 32 and vena cava 33 are shown. In recent studies, it has been shown that plasmapheresis components of this type can be expected to be implanted for up to 2–3 years with the coatings as previously described. Without such coatings, the life may be reduced to up to 18 months. The space between the patient's external skin surface and to the cuff 26 should also be periodically cleansed and flushed with antibacterial solution.

By way of example, a female patient, age 36, weighing 50 kg (110 pounds) having a non-hyper catabolic, residual renal function of 1.5 ml/min (2.2 L/day) plasma urea clearance, and a dietary protein consumption of 0.8 gm/kg/day (just above malnutrition rate) required plasma extraction of 3.375 L/day, equating to an average flow rate of 2.34 ml/min for 24 hours. The system used, however, should be sized for approximately twice the needed flow rate of the largest patient expected to use the system and thus is adaptable to the lifestyle and needs of such a patient. It has also been found that specific sieving coefficient of the plasmapheresis element may be prescribed for differing bandwidths of plasma components up to $9 \times 10^5$ daltons thus permitting extractions of higher molecular weight plasma proteins that may be necessary to extract for immune system disease treatments and other middle molecules thought to be toxins such as Beta 2 microglobulin. Other variables or modifications of the use of the system include refrigeration of the plasma exudate which may be collected and remotely dialyzed, treated and returned to the patient as autologous infusion fluid, or even used by other patients in critical need as practiced in present blood banks. Additionally, with a fluid infusion system shown in FIG. 2, other therapies such as chemotherapy, IPO infusions, insulin infusion, nutritional supplementation, etc. may be used. These as well as other advantages will be evident to those skilled in the art.

What is claimed is:

1. A method of removing toxins from a patient's blood comprising:

implanting a catheter having a plasmapheresis filter element secured on or adjacent to an end thereof within a blood vessel of a patient;

passing a portion of blood plasma to be discarded and containing the toxins to be removed from the patient's blood supply through said filter element and directing said blood plasma along said catheter; and discarding said portion of blood plasma.

2. The method of claim 1, wherein the blood vessel in which said catheter and filter element are implanted is the superior vena cava.

3. The method of claim 1, including securing an end of said catheter opposite said filter element to an elongated flexible tube and directing said blood plasma to be discarded therethrough.

4. The method of claim 3, including providing a collection member and directing said blood plasma to be discarded from said tube to said collection member.

5. The method of claim 3, including providing a one-way valve cooperating with said tube for preventing blood plasma flow from said tube to said catheter.

6. The method of claim 3, including providing a variable flow valve cooperating with said tube for selectively changing the flow rate of blood plasma to be discarded therethrough.

7. The method of claim 4, including providing a variable flow valve cooperating with said tube for selectively changing the flow rate of blood plasma to be discarded therethrough.

8. The method of claim 3, including creating a vacuum within said tube and said catheter for starting and maintaining the flow of blood plasma therethrough.

9. The method of claim 4, including providing a siphon means between said tube and said collection member and using said syphon means to create a vacuum sufficient to start and maintain the flow of blood plasma through said tube to said collection member.

10. The method of claim 4, including providing a suction pump cooperating with said collection member and using said suction pump to create a vacuum sufficient to start and maintain the flow of blood plasma to said collection member.

11. The method of claim 8, including providing a vacuum release valve cooperating with said tube for selectively terminating said vacuum and stopping the flow of blood plasma in said catheter and said tube.

12. The method of claim 1, wherein said catheter is a dual lumen catheter having a first lumen for directing blood plasma to be discarded from the patient and a second lumen for directing fluid other than said blood plasma to be discarded to the patient.

13. The method of claim 12, including providing fluid source containing fluid other than said blood plasma to be discarded to be infused to the patient, and directing said fluid to the patient through said second lumen.

14. The method of claim 4, comprising continuously passing blood plasma to be discarded through said filter element, along said catheter and through said tube to said collection member.

15. The method of claim 7, comprising continuously passing blood plasma to be discarded through said filter element, along said catheter and through said tube to said collection member.

16. The method of claim 15, comprising increasing the flow rate of blood plasma to be discarded during a period of increased patient physical activity and decreasing the flow rate of blood plasma to be discarded during a period of decreased physical activity.

17. The method of claim 13, comprising continuously passing blood plasma to be discarded through said filter element and passing said blood plasma to be discarded from the patient through said first lumen of said catheter, and selectively and periodically continuously directing fluid other than said blood plasma to be discarded from said fluid source to the patient through said second lumen of said catheter.

18. The method of claim 1, comprising providing a plasmapheresis filter element having a sieving coefficient cutoff between $2 \times 10^4$ daltons and $4 \times 10^6$ daltons.

19. The method of claim 14, comprising providing a plasmapheresis filter element having a sieving coefficient cutoff between $2 \times 10^4$ daltons and $4 \times 10^6$ daltons.

20. An apparatus for removing toxins from a patient's blood comprising:

a single lumen catheter having a plasmapheresis filter element secured on or adjacent to an end thereof, said catheter and said filter capable of implantation in a patient's vena cava or jugular vein and for directing blood plasma to be discarded therefrom;

a flexible tube secured to said catheter for receiving and directing blood plasma to be discarded from said catheter, and a one-way valve cooperating therewith along said flexible tube for preventing fluid flow of said plasma to be discarded from returning from said tube to said catheter; and a container cooperating with said tube for receiving and collecting blood plasma from said tube to be discarded.

21. The apparatus of claim 20, wherein said filter element comprises a hollow fiber and/or sheet membrane having a sieving coefficient cutoff of between $2 \times 10^4$ and $4 \times 10^6$ daltons.

22. The apparatus of claim 20, wherein said filter element comprises a hollow fiber and/or sheet membrane having a total outer surface area of 100–500 cm$^2$.

23. The apparatus of claim 21, wherein said filter element comprises a hollow fiber and/or sheet membrane having a total outer surface area of 100–500 cm$^2$.

24. The apparatus of claim 22 wherein the filter membrane has a flux performance of 1 to 15 ml/min/cm$^2$/bar.

25. The apparatus of claim 23 wherein the filter membrane has a flux performance of 1 to 15 ml/min/cm$^2$/bar.

26. The apparatus of claim 20, including a variable flow control valve cooperating with said tube.

27. The apparatus of claim 20, including a syphon device for creating a vacuum in said tube for initiating and maintaining fluid flow therethrough.

28. The apparatus of claim 20, including a vacuum pump cooperating with said tube or said container for creating a vacuum within said tube for initiating fluid flow therethrough.

29. The apparatus of claim 28, wherein said vacuum pump comprises a hand vacuum pump and one or more check valves.

30. The apparatus of claim 27, including a vacuum release valve cooperating with said tube for terminating the flow of fluid therein.

31. The apparatus of claim 28, including a vacuum release valve cooperating with said tube for terminating the flow of fluid therein.

32. An apparatus for removing toxins from a patient's blood comprising:

a dual lumen catheter having a plasmapheresis filter element secured on or adjacent to a first end thereof, said catheter and said filter element capable of implantation in a patient's vena cava or jugular vein, said catheter having a first lumen for directing blood plasma to be discarded from said patient and a second lumen for directing fluid other than said blood plasma to be discarded to said patient;

an infusion fluid flow directing means cooperating with said second lumen of said catheter for directing fluid other than said blood plasma to be discarded to said patient therethrough;

a flexible tube cooperating with said first lumen for directing blood plasma to be discarded from said patient therethrough and a one-way valve cooperating therewith for preventing flow of said blood plasma to be discarded back to said patient; and a container for receiving and collecting blood plasma to be discarded from said tube.

33. The apparatus of claim 32, wherein said filter element comprises a hollow fiber and/or sheet membrane having a sieving coefficient cutoff of between $2 \times 10^4$ and $4 \times 10^6$ daltons.

34. The apparatus of claim 32, wherein said filter element comprises a hollow fiber and/or sheet membrane having a total outer surface area of 100–500 cm$^2$.

35. The apparatus of claim 33, wherein said filter element comprises a hollow fiber and/or sheet membrane having a total outer surface area of 100–500 cm$^2$.

36. The apparatus of claim 33 wherein the filter membrane has a flux performance of 1 to 15 ml/min/cm$^2$/bar.

37. The apparatus of claim 32, including a variable flow control valve cooperating with said tube.

38. The apparatus of claim 32, including a syphon device for creating a vacuum in said tube for initiating and maintaining fluid flow therethrough.

39. The apparatus of claim 32, including a vacuum pump cooperating with said tube or said container for creating a vacuum within said tube for initiating fluid flow therethrough.

40. The apparatus of claim 39, wherein said vacuum pump comprises a hand vacuum pump and one or more check valves.

41. The apparatus of claim 38, including a vacuum release valve cooperating with said tube for terminating the flow of fluid therein.

42. The apparatus of claim 39, including a vacuum release valve cooperating with said tube for terminating the flow of fluid therein.

* * * * *